us008109268B2

(12) United States Patent
Rohde et al.

(10) Patent No.: US 8,109,268 B2
(45) Date of Patent: Feb. 7, 2012

(54) DEVICE FOR DETECTING A GAS VOLUME FLOW

(75) Inventors: Kerstin Rohde, Hamburg (DE); Henning Gerder, Lübeck (DE); Bernd Kellner, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1135 days.

(21) Appl. No.: 11/927,031

(22) Filed: Oct. 29, 2007

(65) Prior Publication Data

US 2008/0167568 A1 Jul. 10, 2008

(30) Foreign Application Priority Data

Jan. 8, 2007 (DE) .................. 10 2007 001 262

(51) Int. Cl.
- A61M 16/00 (2006.01)
- A62B 7/00 (2006.01)
- F16K 31/02 (2006.01)
- G01F 1/66 (2006.01)

(52) U.S. Cl. ............ 128/204.23; 128/204.18; 73/861.27

(58) Field of Classification Search ............ 128/204.18, 128/204.21, 204.23; 73/861.23, 861.25–861.29, 73/861.31; 600/529, 538
See application file for complete search history.

(56) References Cited

U.S. PATENT DOCUMENTS

| 3,810,258 | A | * | 5/1974 | Mathauser ...................... 439/39 |
| 5,253,520 | A |  | 10/1993 | Drexel et al. |
| 5,419,326 | A |  | 5/1995 | Harnoncourt |
| 6,584,862 | B1 | * | 7/2003 | Molenaar .................... 73/861.27 |
| 6,629,934 | B2 | * | 10/2003 | Mault et al. .................... 600/538 |
| 2002/0013536 | A1 |  | 1/2002 | Mault |
| 2003/0065273 | A1 |  | 4/2003 | Mault et al. |
| 2004/0093957 | A1 | * | 5/2004 | Buess et al. ................ 73/861.27 |

FOREIGN PATENT DOCUMENTS

| CN | 2166415 Y | 5/1994 |
| DE | 40 34 176 A1 | 11/1991 |
| DE | 42 22 286 C1 | 5/1994 |
| DE | 102006024363 | 11/2007 |
| EP | 0 647 427 A1 | 4/1995 |
| EP | 0 945 712 A1 | 9/1999 |
| JP | 6310213 | 11/1994 |

* cited by examiner

*Primary Examiner* — Loan Thanh
*Assistant Examiner* — Kathryn D Sheikh
(74) *Attorney, Agent, or Firm* — McGlew and Tuttle, P.C.

(57) ABSTRACT

A device is provided for detecting a gas volume flow, especially for a respirator. The device includes a flow sensor, which surrounds a lumen for guiding the gas volume flow, and the flow sensor has an ultrasound transmitter with a sound generator (20) and an ultrasound receiver. The device has a connection sensor (17, 19), which is designed to detect a connection, especially an installation position or correctness of the connection or both, of the ultrasound transmitter to the transmitter mount and/or a connection of the ultrasound receiver to the receiver mount and to change at least one of its electrical properties as a function of the connection, or to generate a connection signal, which represents the connection, and to output this signal on the output side.

15 Claims, 10 Drawing Sheets

DEVICE FOR DETECTING A GAS VOLUME FLOW

CROSS REFERENCE TO RELATED APPLICATIONS

This application claims the benefit of priority under 35 U.S.C. §119 of German Patent Application DE 10 2007 001 262.6 filed Jan. 8, 2007, the entire contents of which are incorporated herein by reference.

FIELD OF THE INVENTION

The present invention pertains to a device for detecting a gas volume flow, especially a respirator. The device comprises a flow sensor, which surrounds a lumen for guiding the gas volume flow, and the flow sensor has an ultrasound transmitter and an ultrasound receiver. The ultrasound transmitter and the ultrasound receiver are arranged at spaced locations from one another such that the ultrasound receiver can receive ultrasound waves transmitted by the ultrasound transmitter and the ultrasound waves pass through the lumen at least in some sections.

BACKGROUND OF THE INVENTION

To avoid cross infections, the flow sensor is designed as a sensor that can be disinfected and/or replaced in devices known from the state of the art for detecting a gas volume flow by means of a flow sensor, especially in medical devices with a flow sensor. In an inexpensive device for detecting a gas volume flow, the ultrasound transmitter and the ultrasound receiver must therefore be separated from the flow sensor for the replacement of the flow sensor.

An ultrasound spirometer, which has a replaceable flow sensor, is known from DE 42 22 286 C1; the flow sensor has a measuring tube, into which a sterile, easy-to-replace tube can be inserted in an accurately fitting manner. The sterile tube is inserted in an accurately fitting manner and has at a transition to an ultrasound measuring window, which is permeable to sound waves but extensively impermeable to microorganisms and other contaminants. The measuring windows may be formed by a foam, by an elastomer, or by a very thin plate, especially a Mylar film.

A device for measuring the flow velocity of a gas in a medical application by means of ultrasound run time measurement with a measuring tube and two ultrasound converters that can be inserted into the measuring tube is known from DE 101 56 854 A1. The ultrasound converters are separated from an interior space of the measuring tube by means of membranes. The membranes are of a gas-tight design according to the present invention and inserted into the measuring tube such that the latter forms a gas-tight tube connection. The ultrasound converters separably connected to the measuring tube have a flush contact with the membranes.

Devices known from the state of the art with a flow sensor for detecting a gas volume flow have ultrasound converters, which can detect a flow velocity of the gas flow, especially by means of doppler interferometry. The device may comprise for this an analysis unit, which is connected to the ultrasound transmitter and the ultrasound receiver and is designed to detect a sound wavelength and/or sound run time of an ultrasound transmitted by the ultrasound transmitter and received by the ultrasound receiver.

SUMMARY OF THE INVENTION

It was recognized according to the present invention that the accuracy of a measurement result depends on the connection and the arrangement of the ultrasound converters in relation to one another. Furthermore, it was recognized that wear of a mount for an ultrasound converter separably connected to a measuring section of the gas line causes errors in measurement in case of wear of the mount.

The basic object of the present invention is to provide an improved device for detecting a gas volume flow.

This object is accomplished by a device of the type according to the present invention, in which the flow sensor has a transmitter mount for the ultrasound transmitter and a receiver mount for the ultrasound receiver, and the transmitter mount is designed to be separably connected to the ultrasound transmitter, and the receiver mount is designed to be separably connected to the ultrasound receiver. The device has a connection sensor, which is designed to detect a connection, especially an installation position or correctness of the connection or both, of the ultrasound transmitter to the transmitter mount, especially in a contactless manner, and/or to detect a connection of the ultrasound receiver to the receiver mount, and to change at least one of its electric properties as a function of the connection, or to generate a connection signal, which represents the connection, and to output this on the output side. Correct assembly of an ultrasound transmitter and/or of an ultrasound receiver with the transmitter mount or with the receiver mount of the flow sensor can advantageously be performed by means of the connection sensor in a device of the above-described type. The connection sensor may thus advantageously be a positioning sensor for the ultrasound transmitter. For example, the device may have a connecting device, which is connected to the ultrasound transmitter and to the connection sensor and can activate the ultrasound sensor and/or a gas pump for generating the gas volume flow as a function of the connection signal.

An ultrasound transmitter, which has a radiation characteristic with non-uniform distribution in space, may also be advantageously used due to the connection sensor. For example, an ultrasound transmitter can have a radiation distribution, especially a sound intensity distribution of a radiated sound as a function of a dihedral angle, which distribution represents a gap function and therefore has a lobe-shaped radiation characteristic in at least one transverse direction to the direction of sound propagation.

Exemplary embodiments for an electric property of a connection sensor are an ohmic resistance, a capacity or an inductivity or a combination of these.

In a preferred embodiment, the connection sensor is a magnetic sensor, which is connected to the ultrasound transmitter and can detect a magnetic field in the area of the transmitter mount. The connection sensor may be formed in this embodiment by a Hall sensor or a reed contact. The flow sensor may have for this, in the area of the transmitter mount, a permanent magnet, which is designed to generate a permanent magnetic field. The permanent field is, for example, a ferromagnet. The position of assembly of an ultrasound transmitter with a mount for the ultrasound transmitter can advantageously be selected correctly due to a connection sensor. It is thus advantageously possible to use an ultrasound transmitter with a radially symmetrical housing.

In a preferred embodiment, the ultrasound receiver is an ultrasound converter, which can be additionally operated as an ultrasound transmitter, and/or the ultrasound transmitter is an ultrasound converter, which can additionally be operated as an ultrasound receiver. Reciprocal detection of a sound wavelength or a sound run time can be advantageously carried out as a result. Furthermore, erroneous assembly of a detection or measuring device can be advantageously detected by the reciprocal detection.

In an advantageous embodiment, the transmitter mount and/or the receiver mount has a conically shaped contact surface. Sufficient sealing of a contact surface of the ultrasound transmitter with a contact surface of the transmitter mount or of the ultrasound receiver with the receiver mount can advantageously be ensured by the conically shaped contact surface. Correct alignment of the ultrasound transmitter and/or the ultrasound receiver can also be advantageously ensured by means of a conically shaped contact surface.

An ultrasound sensor can preferably generate and transmit ultrasound waves at a frequency in the range of 350 kHz to 500 kHz and preferably between 400 kHz and 450 kHz.

In a preferred embodiment, the connection sensor is designed as an ultrasound transmitter and receiver pair to detect a sound wavelength. As a result, a cross section of a gas line used can be advantageously detected. For example, the gas line, especially the flow sensor, may be formed by a measuring cell. The measuring cell may advantageously be designed as a sterilizable cell and more advantageously as a sterile disposable article. Due to the detection of the sound wavelength, a measuring cell intended for adults can be advantageously distinguished from a measuring cell intended for respirating newborns. The device may advantageously have for this purpose a measuring cell discriminator, which is designed to generate an output signal, which corresponds to a type of measuring cell used, as a function of a detected sound wavelength.

The present invention also pertains to a respirator with a device of the above-described type. The respirator may advantageously have a respirator for generating an inspiratory gas flow and an expiratory gas flow. The respirator may advantageously have a compressor, especially a radial compressor, for generating the expiratory and/or inspiratory gas flow. The respirator may advantageously have two or three flow sensors. For example, the respirator may have a flow sensor for detecting an expiratory gas flow, a flow sensor for detecting an inspiratory gas flow and preferably another flow sensor for detecting a gas flow in a lumen used jointly for the expiration and inspiration.

The present invention also pertains to a flow sensor, especially for a respirator. The flow sensor has a transmitter mount for an ultrasound transmitter and a receiver mount for an ultrasound receiver, the transmitter mount being designed to be separably connected to the ultrasound transmitter, and the receiver mount being designed to be separably connected to the ultrasound receiver. The transmitter mount and/or the receiver mount preferably has a conically shaped contact surface. Exact assembly of an ultrasound converter with a mount for the ultrasound converter can be performed due to the conically shaped contact surface. The probability of tilted assembly is advantageously also reduced by the conically shaped contact surface. A sensor element for a connection sensor, which element can be detected magnetically, is preferably arranged in the area of the transmitter mount and/or the receiver mount.

The present invention will be described below on the basis of figures and additional exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
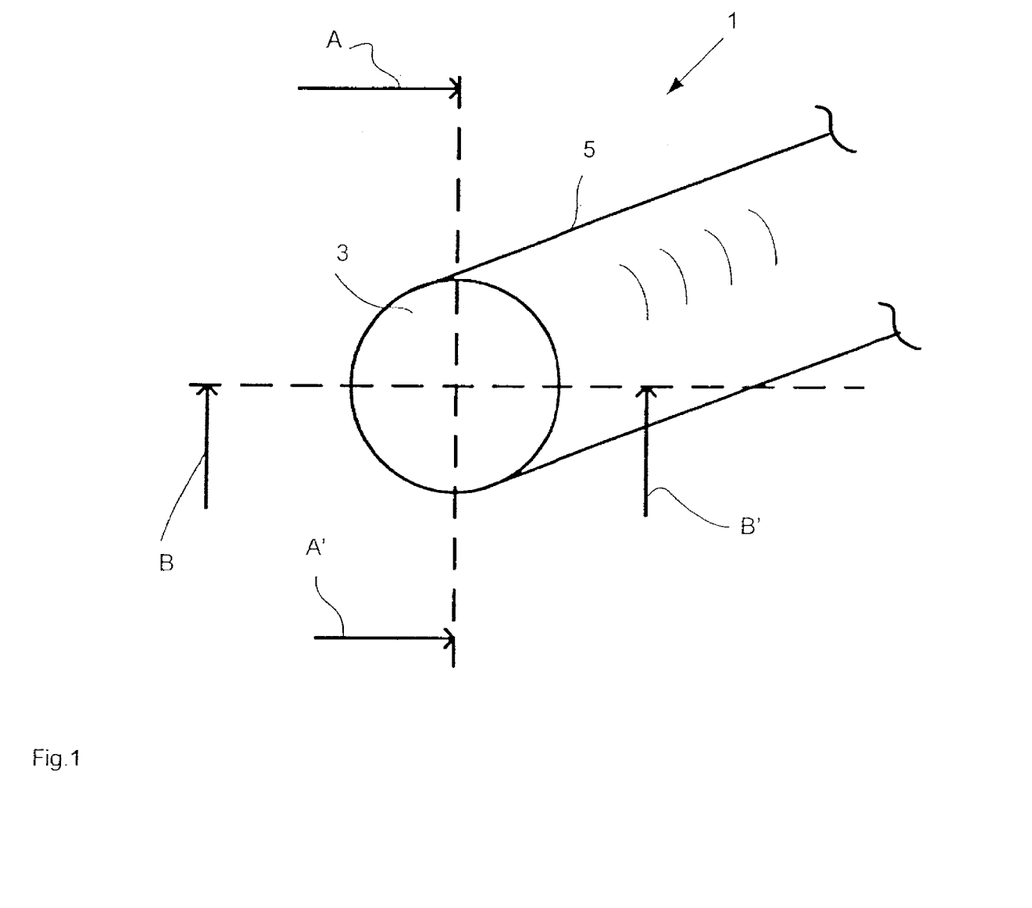
FIG. 1 is a schematic view showing an end section of an ultrasound transmitter.

Referring to the drawings in particular FIG. 1 schematically shows an exemplary embodiment of an end section of an ultrasound transmitter 5. The ultrasound transmitter 5 has a cylindrically shaped housing. The ultrasound transmitter 5 has a surface 3, which is capable of oscillating and which forms in this exemplary embodiment one end of the cylindrical end section of the ultrasound transmitter 5. The oscillating surface 3 (capable of vibrating) has a round surface limitation, in particular, a circular surface limitation in this exemplary embodiment. A broken section line to a section A, A' is shown, which extends in a plane formed by the surface 3 capable of oscillating. Also shown is a broken section line to a section B, B', which extends at right angles to the broken section line of section A, A' and in the plane formed by the surface 3 capable of oscillating. A directional diagram of an intensity distribution of the airborne sound generated by the ultrasound transmitter 5 is shown in FIGS. 2 and 3.

Figure 2:
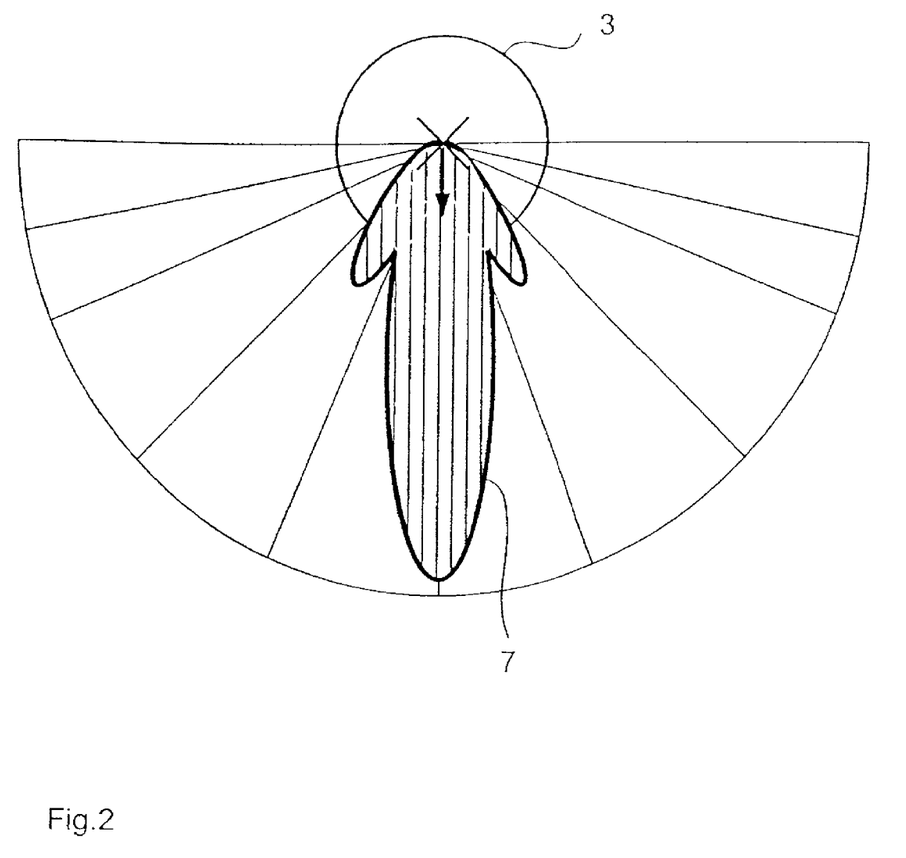
FIG. 2 is a schematic directional diagram view of a sound intensity distribution of an ultrasound transmitter shown in FIG. 1.

FIG. 2 shows a directional diagram of a sound intensity distribution of an airborne sound radiated by the ultrasound transmitter 5 shown in FIG. 1 in a section plane that extends at right angles to the surface 3 capable of oscillating and in which the section line of the section B, B' in FIG. 1 extends. The intensity distribution 7 shown in FIG. 2 represents a sound intensity generated by the surface 3 capable of oscillating as a function of a dihedral angle. Clearly recognizable is a narrow lobe shape of the intensity distribution 7, which represents a gap function with one main lobe and two secondary lobes.

Figure 3:
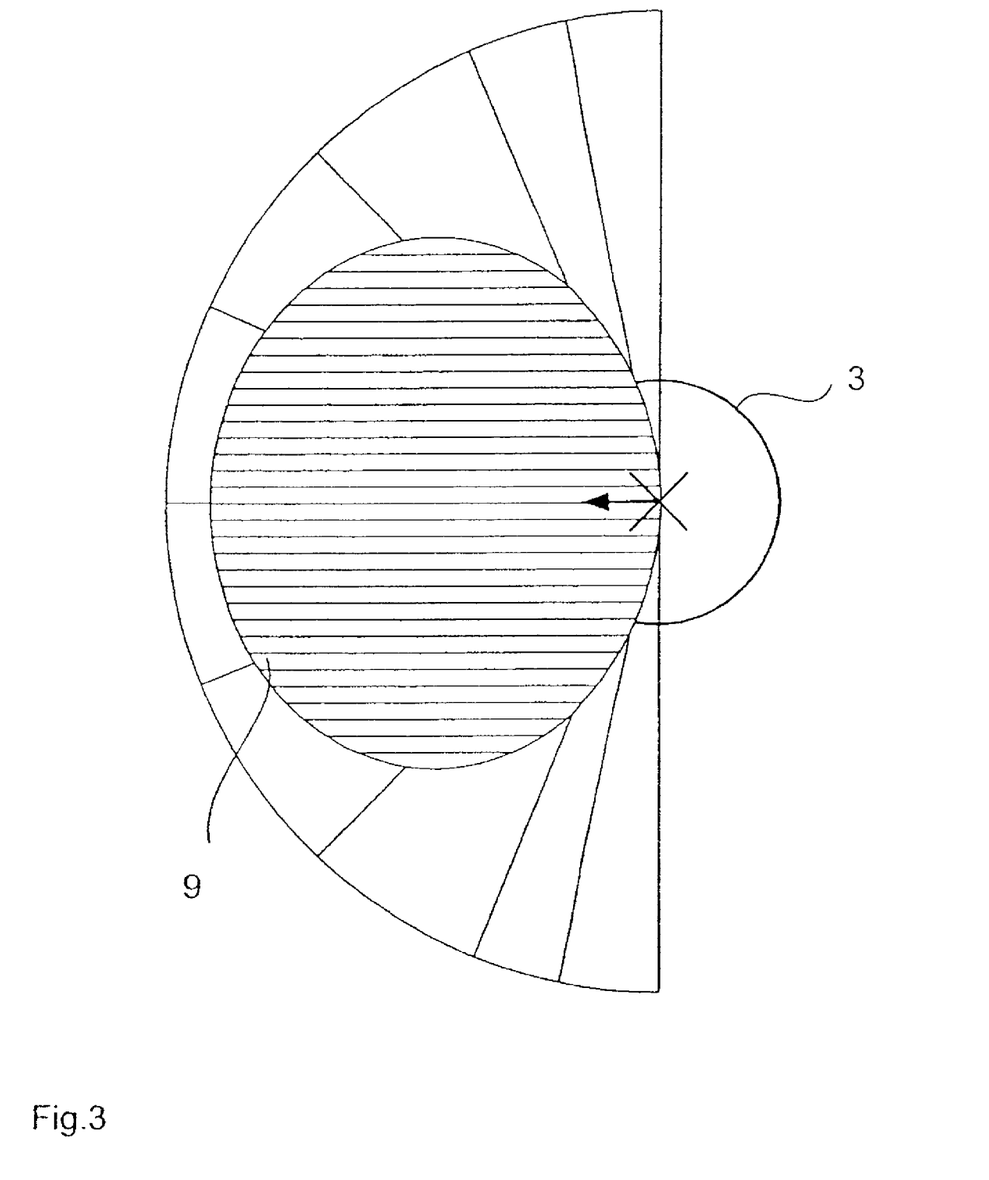
FIG. 3 is a schematic directional diagram view of a sound intensity distribution of the ultrasound transmitter shown in FIG. 1.

FIG. 3 schematically shows a directional diagram of a sound intensity distribution 9 of the airborne sound generated by the surface 3 capable of oscillating in FIG. 1 in a section plane that extends at right angles to the surface 3 capable of oscillating and in which the section line of section A, A' is located. Clearly recognizable is an omnidirectional characteristic of the sound intensity distribution 9, which represents a sound intensity generated by the surface capable of oscillating as a function of a dihedral angle.

Figure 4:
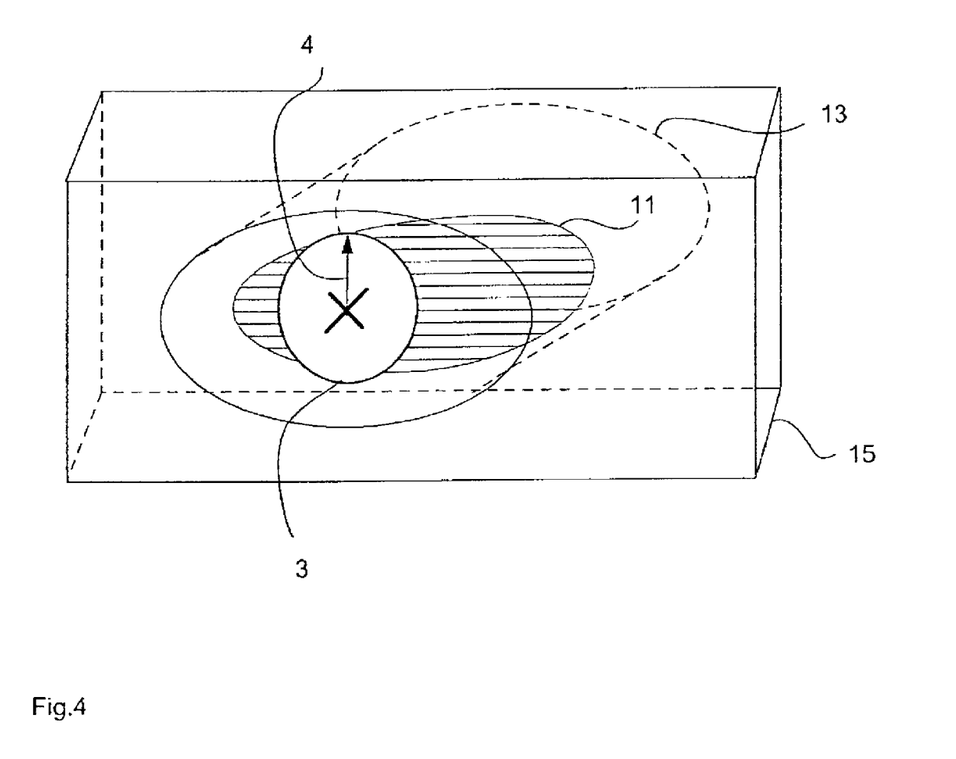
FIG. 4 is a schematic view showing an exemplary embodiment of a lumen of a gas line for guiding a gas volume flow in the area of a flow sensor.

FIG. 4 schematically shows an exemplary embodiment of a lumen 15, especially of a gas line or of a flow sensor, for guiding a gas volume flow in the area of a flow sensor. Shown is the surface 3 capable of oscillating of the ultrasound transmitter 5 shown in FIG. 1. Also shown is a receiving surface 13, in which the airborne sound transmitted by the surface 3 capable of oscillating can be received. For example, an ultrasound receiver may be arranged in the receiving surface 13. Also shown is a section 11 through the intensity distribution of the airborne sound radiated by the surface 3 capable of oscillating, which distribution has an elliptically shaped circumference. The surface 3 capable of oscillating is directed in circumferential rotation about the longitudinal axis of the ultrasound transmitter 5, which axis extends at right angles to the surface 3 capable of oscillating, such that the elliptically shaped section surface of section 11 is imaged, beginning from the surface 3 capable of oscillating, onto the receiving surface 13. The airborne sound transmitted by the surface 3 capable of oscillating can thus be received within the receiving surface 13. A direction arrow 4 of the surface 3 capable of oscillating is shown as well.

Figure 5:
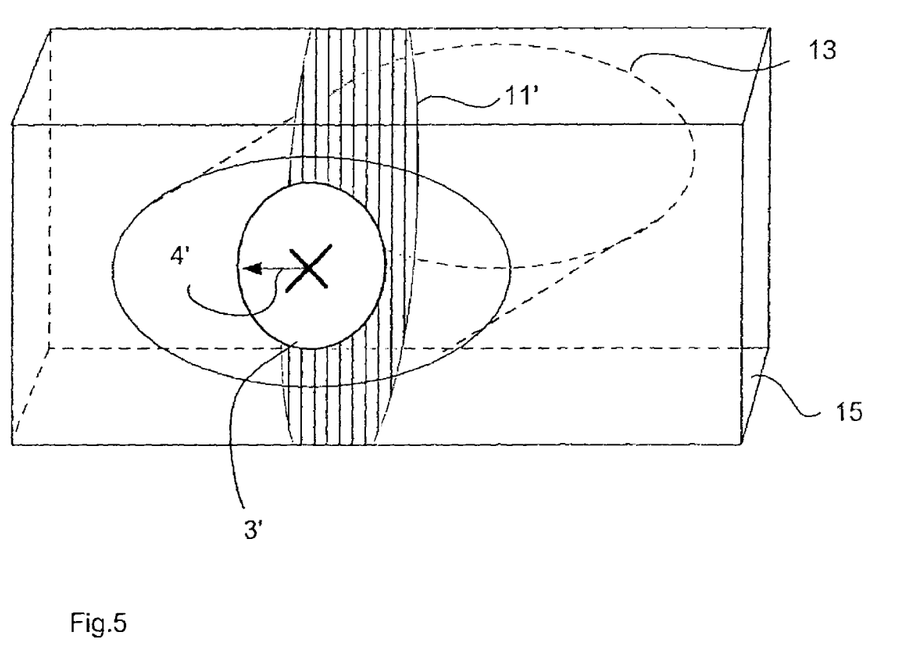
FIG. 5 is a schematic view showing a surface capable of oscillating, which is shown in FIG. 4, in a rotated arrangement.

FIG. 5 schematically shows the lumen 15 shown in FIG. 4 and the surface 3 capable of oscillating, which is shown in FIG. 4, and which is rotated by 90° about the longitudinal axis of the ultrasound transmitter 5 shown in FIG. 1 compared to the surface 3 capable of oscillating, which is shown in FIG. 4. The intensity distribution shown in FIGS. 3 and 4 is likewise rotated now by 90°, which is shown by the rotated sectional arrangement 11' of the section 11 shown in FIG. 4. The airborne sound transmitted by the surface 3 capable of oscillating is no longer radiated completely onto the receiving surface 13, and undesired reflections may therefore develop in this exemplary embodiment on the bordering surfaces of a gas guiding housing surrounding the lumen 15. These undesired reflections may distort the result of the detection and/or measurement of a gas volume flow flowing through the lumen 15 by means of ultrasound or make detection impossible. The lumen 15 shown in FIG. 4 and FIG. 5 is designed with a rectangular, especially square cross section in this exemplary embodiment to illustrate the geometric conditions. Unlike as shown in FIGS. 4 and 5, a round cross section of a lumen for guiding a gas volume flow is conceivable and advantageous as well.

Figure 6:
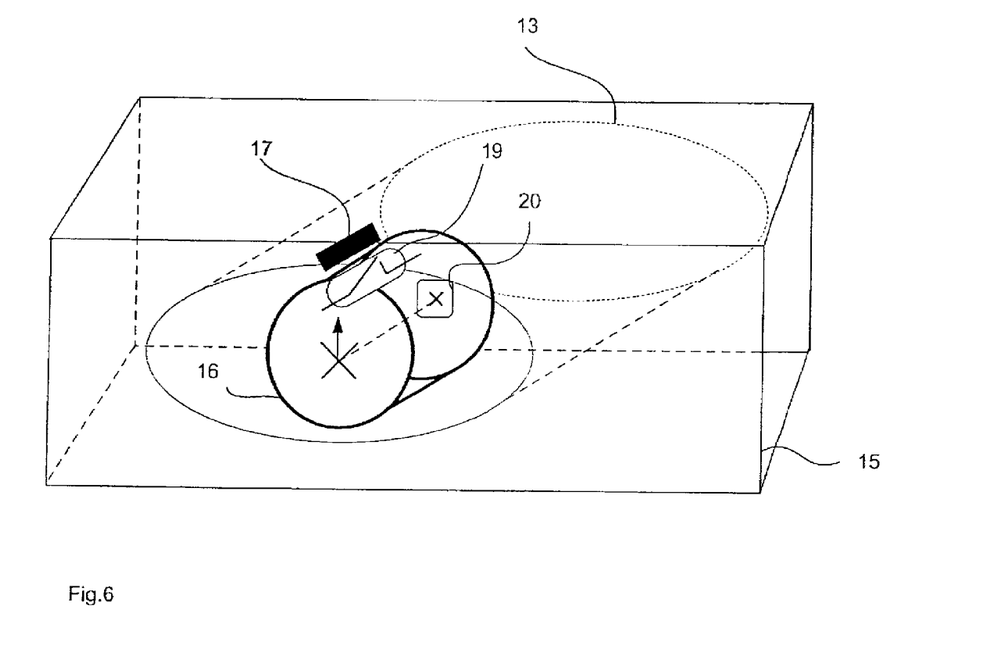
FIG. 6 is a schematic view showing the lumen shown in FIG. 4 and in FIG. 5 together with an ultrasound transmitter.

FIG. 6 schematically shows the lumen 15 shown in FIG. 4 and in FIG. 5 and the receiving surface 13. A cylindrically shaped ultrasound transmitter 16 is shown. The ultrasound transmitter 16 has an acoustic sound generator 20. The ultrasound transmitter 16 also has a reed contact 19. Also shown is a magnet 17, especially a ferromagnet, which is connected, for example, to a housing guiding the lumen 15, and which is designed to generate a magnetic field such that a reed contact 19 arranged in the range of action of the magnet 17 can be closed in an electrically effective manner.

The reed contact 19 is arranged in the area of an outer circumference of the cylindrically shaped ultrasound transmitter 16. The reed contact 19 is thus located at a spaced location radially outwardly from a longitudinal axis extending centrally through the ultrasound transmitter 16. When the ultrasound transmitter 16 is moved by rotation about the longitudinal axis and by positioning along the longitudinal axis, the reed contact 19 can close in an electrically effective manner when the reed contact 19 is brought—by corresponding motion of the ultrasound transmitter 16—into the range of action of the magnet 17. Exact positioning of the ultrasound transmitter 16 can thus be ensured, especially when activation of the acoustic sound generator 20 takes place as a function of the electrically effective closing of the reed contact 19.

Figure 7:
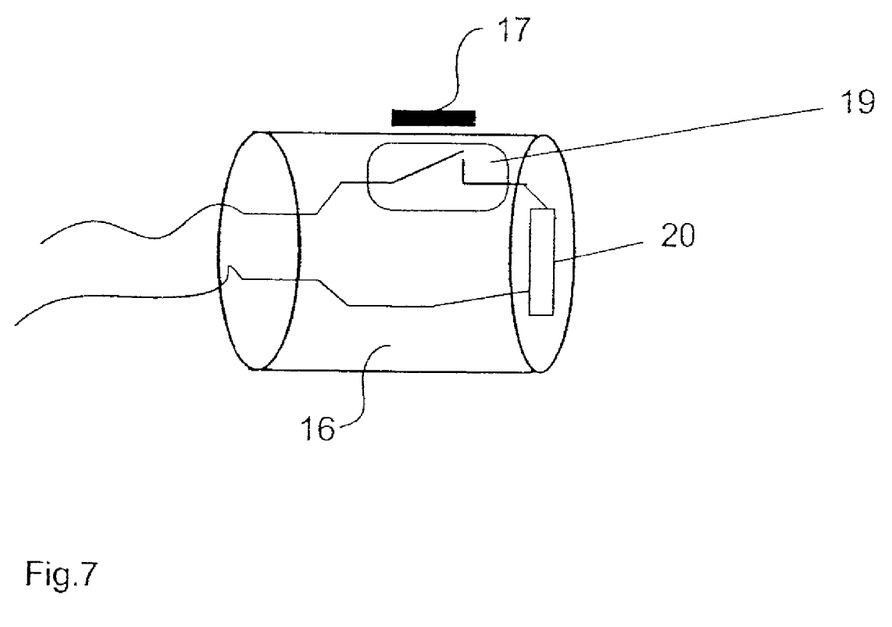
FIG. 7 is a schematic view showing the ultrasound transmitter shown in FIG. 6 with an acoustic sound generator and a reed contact.

FIG. 7 schematically shows the ultrasound transmitter 16 shown in FIG. 6 with the acoustic sound generator 20 and with the reed contact 19, which is arranged in the range of action of the magnet 17. The acoustic sound generator 20 is connected electrically in series with the reed contact 19. The acoustic sound generator can thus be activated as a function of the closing of the reed contact 19.

Figure 8:
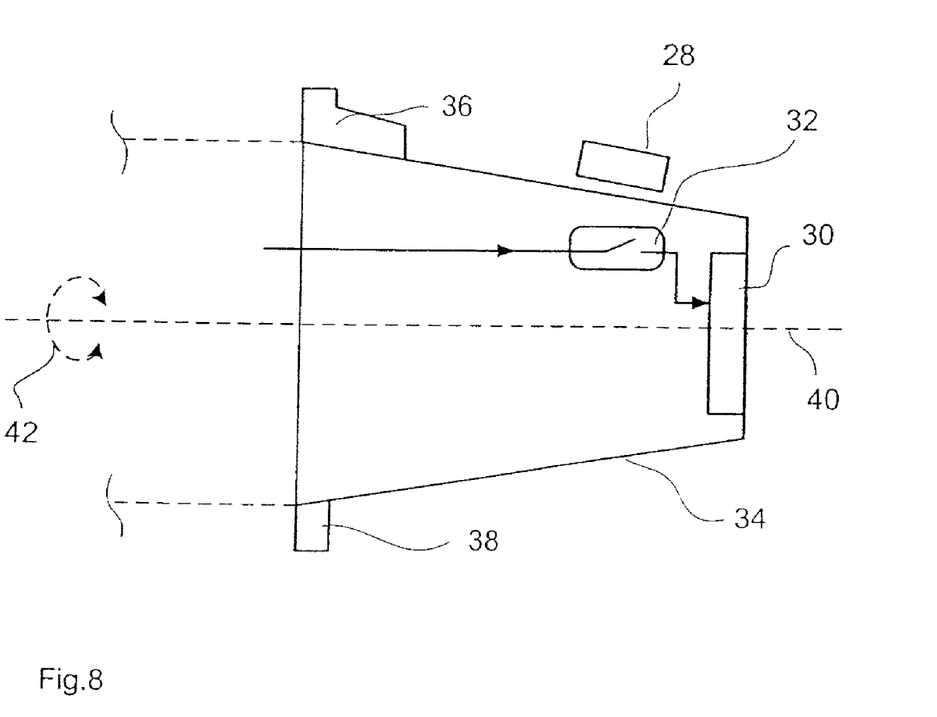
FIG. 8 is a schematic longitudinal sectional view showing an exemplary embodiment of an ultrasound transmitter.

FIG. 8 schematically shows a longitudinal sectional view of an exemplary embodiment of an ultrasound transmitter 34. The ultrasound transmitter 34 has a conical design, such that an external diameter of a housing of the ultrasound transmitter 34 decreases linearly along a longitudinal axis 40. The ultrasound transmitter 34 has a round cross section and thus forms a section of a circular cone. An acoustic sound generator 30 is arranged in the area of a narrower end of the ultrasound transmitter 34. The acoustic sound generator 30 is connected in series with a reed contact 32, the reed contact 32 being located at a spaced location radially outwardly from the centrally extending longitudinal axis 40 and being arranged in the area of the circumference of the ultrasound transmitter 34. Also shown is a magnet 28, which is arranged outside the ultrasound transmitter 34 and is designed to electrically close the reed contact 32 when the reed contact 32 is located in the range of action of the magnet 28. The ultrasound transmitter 34 can thus be activated as a function of the electrically effective closing of the reed contact 32, especially as a function of the magnetic field acting on the reed contact. The activated ultrasound transmitter 34 can generate and transmit an airborne sound in the ultrasound frequency range.

The ultrasound transmitter 34 has a groove 36 in the area of a broader end. The groove 36 is intended for introduction into a corresponding recess of a housing for guiding a gas volume flow. The recess may be designed for this such that a rotary motion 42 of the ultrasound transmitter 34 about the longitudinal axis 40 can take place in a predetermined angle range, for example, 30, so that the ultrasound transmitter 34 can already be pre-positioned by a mechanical coding formed by means of the groove 36. The pre-positioning may be performed, for example, when introducing the ultrasound transmitter 34 into a corresponding mount of a flow sensor for detecting a gas volume flow along the longitudinal axis 40. Exact alignment of the ultrasound transmitter 34 in the circumferential direction can take place by a further rotary motion 42 of the ultrasound transmitter 34 about the longitudinal axis 40.

Figure 9:
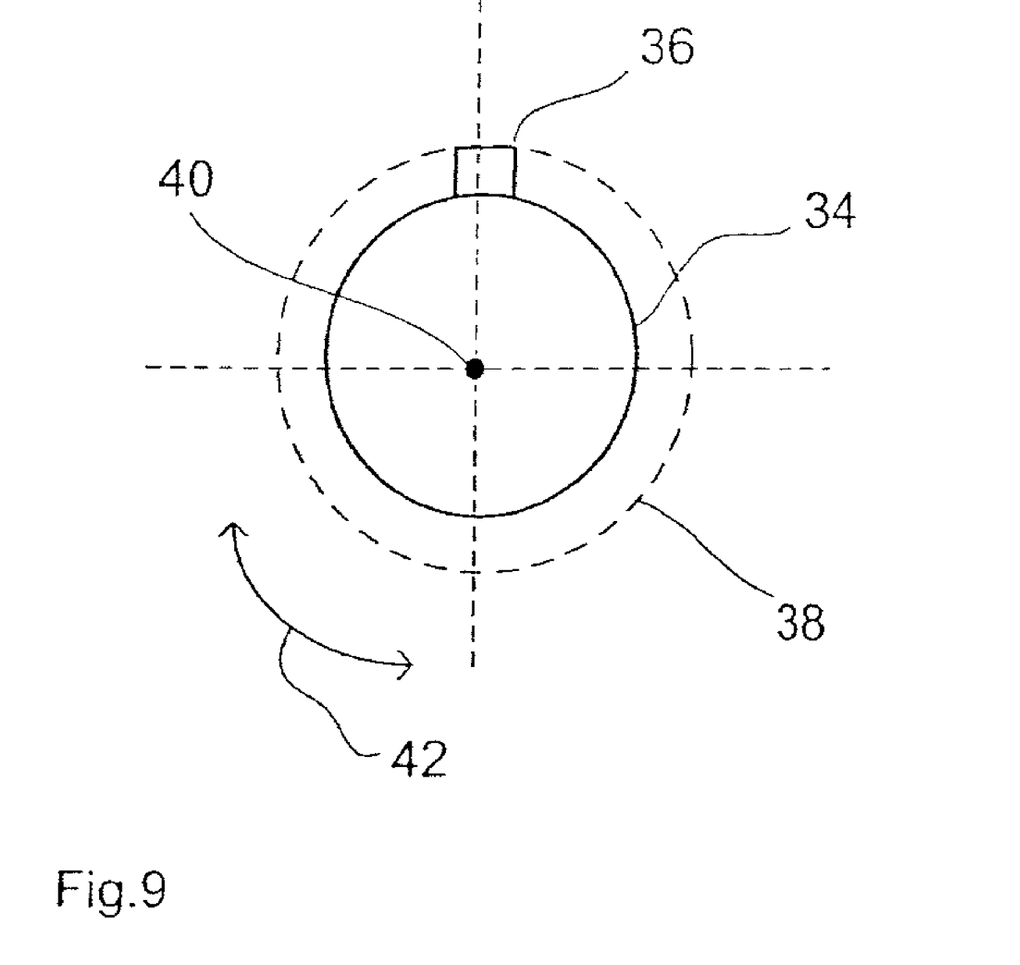
FIG. 9 is a schematic view showing a top view of a broader end of the ultrasound transmitter shown in FIG. 8.

FIG. 9 schematically shows a top view of the broader end of the ultrasound transmitter 34. The groove 36, the longitudinal axis 40 and the rotary motion 42 are shown. A closed groove 38 extending about the longitudinal axis 40 is also shown by broken line. Such a circumferential groove 38 may be used as a coding for making a distinction between the ultrasound transmitter and the ultrasound receiver. The circumferential groove 38 is also shown in FIG. 8. For example, an ultrasound receiver may have the closed groove 38, and the ultrasound transmitter may have the groove 36.

Figure 10:
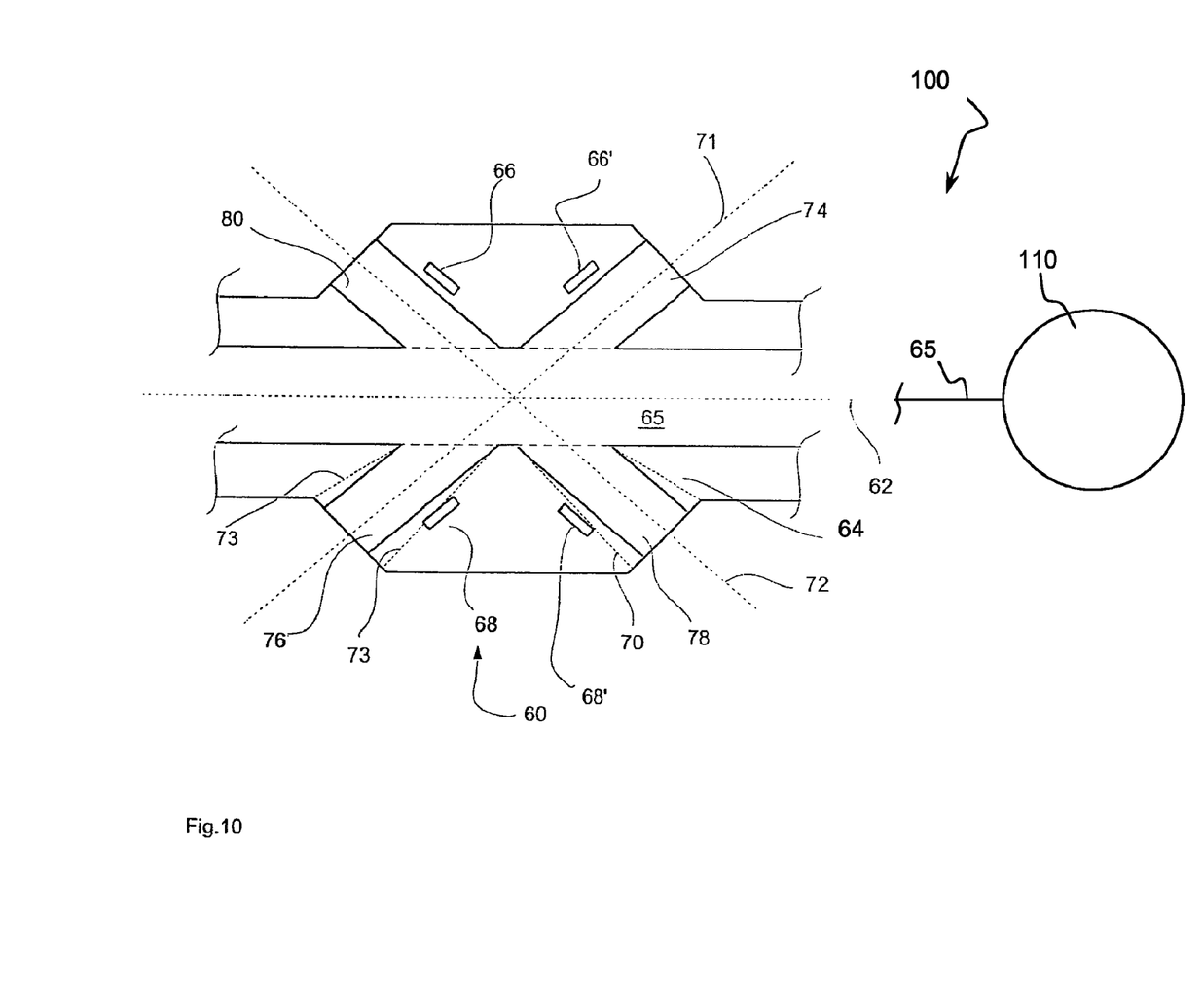
FIG. 10 is a schematic view showing an exemplary embodiment of a flow sensor.

FIG. 10 schematically shows an exemplary embodiment of a flow sensor 60, of a respirator 100, in a longitudinal sectional view. The flow sensor 60 has a housing 64, which surrounds a lumen 65 of the respirator 100 and is designed to guide a gas volume flow (breathing gas) in the lumen 65. The respirator 100 may advantageously have a compressor 110, for generating the expiratory and/or inspiratory gas flow. The respirator 100 may advantageously have two or three flow sensors 60. The housing 64 may form, for example, a measuring cell designed as a disposable article. The housing 64 of the flow sensor 60 has at least one transmitter mount 76 for an ultrasound transmitter and a receiver mount 74 for an ultrasound receiver. The housing 64 also has magnets 68 and 68', which are arranged in the area of the mount 76 for an ultrasound transmitter. The housing 64 also has a transmitter mount 78 for another ultrasound transmitter and a receiver mount 80 for receiving another ultrasound receiver. A conical contact surface 73 of the transmitter mount 78 and a conical mounting surface 70 of the receiver mount 78 are also shown as examples. For example, the conical mounting surface 70 may be designed such that the ultrasound transmitter 34 shown in FIG. 8 can be introduced into the transmitter mount 78 along the longitudinal axis 40 and along a longitudinal axis 72 extending through the transmitter mount 78.

The lumen 65 extends along a longitudinal axis 62. A gas volume flow guided in the lumen 65 can thus be moved along the longitudinal axis 62. The transmitter mount 78 and the receiver mount 80 are arranged opposite each other along the longitudinal axis 72 such that the transmitter mount 78 and the receiver mount 80 enclose between them the lumen 65 at least in some sections. An ultrasound transmitter arranged in the transmitter mount 78 can thus transmit ultrasound waves through the lumen 65, and these ultrasound waves can be received by a receiver arranged in the receiver mount 80. A magnet 66 or 66' is arranged in the area of the receiver mount 80. As a result, an ultrasound converter, which can act both as an ultrasound transmitter and as an ultrasound receiver, can be arranged in the receiver mount 80. A longitudinal axis 71 extends through the receiver mount 74 along the longitudinal axis thereof and through the transmitter mount 76 along the longitudinal axis thereof. The longitudinal axis 71 and the longitudinal axis 72 are arranged at a predetermined angle in relation to one another. The longitudinal axis 71 and the longitudinal axis 72 are preferably arranged at right angles to one another. The longitudinal axis 71 forms a predetermined angle with the longitudinal axis of 62 of the lumen 65. The longitudinal axis 72 forms a predetermined angle with the longitudinal axis 62 of the lumen 65. The predetermined angle is, for example, smaller than or equals 90°. As a result, ultrasound waves which are transmitted in the area of the transmitter mount 76 pass through the lumen 65 with a component in the transverse direction and reach the receiver mount 74 and an ultrasound receiver arranged there after passing through some sections of the lumen 65. Due to the crossover arrangement of the longitudinal axes 71 and 72, ultrasound waves transmitted along these can pass through the lumen 65 in mutually different directions.

The magnets 66, 66', 68, 68' are used, in conjunction with the reed contacts 19, not shown in FIG. 10, for positioning ultrasound transmitters and ultrasound receivers, likewise not shown. It is possible to equip only the transmitting elements with reed contacts in a four-converter arrangement, so that it can be unambiguously recognized when starting up the system whether, for example, two transmitting elements are located opposite each other due to incorrect assembly. Regardless of the contactless detection, galvanic detection of the connection by means of touching is possible as well, for which a connection sensor can have at least one galvanic contact intended for touching.

While specific embodiments of the invention have been shown and described in detail to illustrate the application of the principles of the invention, it will be understood that the invention may be embodied otherwise without departing from such principles.

What is claimed is:
1. A device for detecting a gas volume flow, the device comprising:
   a lumen for guiding the gas volume flow;
   a flow sensor surrounding said lumen, said flow sensor including an ultrasound transmitter and an ultrasound receiver, said ultrasound transmitter being positionable independently and separately from said ultrasound receiver
   a mount associated with said flow sensor, said mount including a transmitter mount defining a transmitter space for receiving said ultrasound transmitter for mounting said ultrasound transmitter, said transmitter mount for separably connecting said mount to said ultrasound transmitter independently of and separately from said ultrasound receiver, and said mount including a receiver mount defining a receiver space for receiving said ultrasound receiver for mounting said ultrasound receiver, said receiver mount for separably connecting said mount to said ultrasound receiver independently of and separately from said ultrasound transmitter, said ultrasound transmitter being arranged in said transmitter space by said transmitter mount at a spaced location from said ultrasound receiver, in said receiver space, such that said ultrasound receiver can receive ultrasound waves transmitted by said ultrasound transmitter and the ultrasound waves pass through said lumen at least in some sections, said mount including a connection sensor for detecting at least one of a physical connection position between said ultrasound transmitter and said transmitter mount and a physical connection position between said ultrasound receiver and said receiver mount, said connection sensor changing at least one electrical property as a function of the physical connection position detected, or generating a connection signal, which represents the physical connection position detected, and providing an output of said at least one electrical property or said connection signal.

2. A device in accordance with claim 1, wherein said connection sensor is a magnetic sensor, including a magnetic sensor part connected to at least one of said ultrasound transmitter and said ultrasound receiver, said magnet sensor for detecting a magnetic field in the area of said transmitter mount and/or said receiver mount.

3. A device in accordance with claim 1, wherein said ultrasound receiver is an ultrasound converter for operation as an ultrasound transmitter and an ultrasound receiver and/or said ultrasound transmitter is an ultrasound converter for operation as an ultrasound receiver and an ultrasound transmitter.

4. A device in accordance with claim 1, wherein at least one of said transmitter space of said transmitter mount and said receiver space of said receiver mount has a conically shaped contact surface.

5. A device in accordance with claim 1, wherein said connection sensor detects said at least one of a physical connection position between said ultrasound transmitter and said transmitter mount and a physical connection position between said ultrasound receiver and said receiver mount without electrical energy passing between said ultrasound transmitter and said transmitter mount and without electrical energy passing between said ultrasound receiver and said receiver mount.

6. A flow sensor comprising:
   an ultrasound transmitter;
   an ultrasound receiver that is separate from said ultrasound transmitter and is positionable independently and separately from said ultrasound receiver;
   a transmitter mount defining a transmitter receiving space for receiving said ultrasound transmitter;
   a receiver mount defining a receiver receiving space for receiving said ultrasound receiver, wherein said transmitter mount is separably connected to said ultrasound transmitter independently of said ultrasound receiver and said receiver mount is separably connected to said ultrasound receiver independently of said ultrasound transmitter, at least one of said transmitter mount transmitter receiving space and said receiver mount receiver receiving space having a conically shaped contact surface and at least one of said ultrasound transmitter and said ultrasound receiver having a complementary conically shaped contact surface cooperating with said conically shaped contact surface; and a connection sensor for detecting at least one of a physical connection position between said ultrasound transmitter and said transmitter mount and a physical connection position between said ultrasound receiver and said receiver mount, said connection sensor changing at least one electrical property as a function of the physical connection position detected, or generating a connection signal, which represents the physical connection position detected, and providing an output of said at least one electrical property or said connection signal.

7. A flow sensor in accordance with claim 6, wherein said connection sensor is a magnetic sensor, including a magnetic sensor part connected to at least one of said ultrasound transmitter and said ultrasound receiver, said magnet sensor for detecting a magnetic field in the area of said transmitter mount and/or said receiver mount.

8. A flow sensor in accordance with claim 6, wherein said transmitter mount and said receiver mount cooperate to form a lumen receiving region, said lumen for guiding a gas volume flow, said transmitter mount and said receiver mount positioning said ultrasound transmitter and said ultrasound receiver relative to said lumen receiving region with said ultrasound transmitter being arranged at a spaced location from said ultrasound receiver such that said ultrasound receiver can receive ultrasound waves transmitted by said ultrasound transmitter and the ultrasound waves pass through said lumen at least in some sections.

9. A flow sensor in accordance with claim 6, wherein said connection sensor detects said at least one of a physical connection position between said ultrasound transmitter and said transmitter mount and a physical connection position between said ultrasound receiver and said receiver mount without electrical energy passing between said ultrasound transmitter and said transmitter mount and without electrical energy passing between said ultrasound receiver and said receiver mount.

10. A respirator comprising:
a lumen defining a gas flow path for guiding a breathing gas volume flow;
an ultrasound transmitter and an ultrasound receiver, said ultrasound transmitter being separate from said ultrasound transmitter and being positionable independently and separately from said ultrasound receiver, said ultrasound transmitter and an ultrasound receiver cooperating to form a flow sensor; and
a flow sensor housing surrounding said lumen, said flow sensor housing comprising a mount associated with said flow sensor, said mount including a transmitter mount defining a transmitter space with an access opening to the transmitter space accessible from outside said flow sensor housing, said transmitter mount for receiving said ultrasound transmitter from outside said flow sensor housing and for separably mounting said ultrasound transmitter in said transmitter space independently of and separately from said ultrasound receiver such that said ultrasound transmitter is directed toward said lumen, and said mount including a receiver mount defining a receiver space with an access opening to the receiver space accessible from outside said flow sensor housing, said receiver mount for receiving said ultrasound receiver from outside said flow sensor housing and for separably mounting said ultrasound receiver in said receiver space independently of and separately from said ultrasound transmitter such that said ultrasound receiver is directed toward said lumen at a spaced location from said ultrasound transmitter, such that said ultrasound receiver can receive ultrasound waves transmitted by said ultrasound transmitter and the ultrasound waves pass through said lumen at least in some sections, said mount including a connection sensor for detecting at least one of a physical connection position of said ultrasound transmitter in said transmitter space and a physical connection position of said ultrasound receiver in said receiver space, said connection sensor changing at least one electrical property as a function of the physical connection position detected, or generating a connection signal, which represents the physical connection position detected, and providing an output of said at least one electrical property or said connection signal.

11. A respirator in accordance with claim 10, wherein said connection sensor is a magnetic sensor, including a magnetic sensor part connected to at least one of said ultrasound transmitter and said ultrasound receiver, said magnet sensor for detecting a magnetic field in the area of said transmitter mount and/or said receiver mount.

12. A respirator in accordance with claim 10, wherein said connection sensor detects said at least one of a physical connection position between said ultrasound transmitter and said transmitter mount and a physical connection position between said ultrasound receiver and said receiver mount without electrical energy passing between said ultrasound transmitter and said transmitter mount and without electrical energy passing between said ultrasound receiver and said receiver mount.

13. A respirator in accordance with claim 10, wherein said ultrasound receiver is an ultrasound converter for operation as an ultrasound transmitter and an ultrasound receiver and/or said ultrasound transmitter is an ultrasound converter for operation as an ultrasound receiver and an ultrasound transmitter.

14. A respirator in accordance with claim 10, wherein at least one of said transmitter space of said transmitter mount and said receiver space of said receiver mount has a conically shaped contact surface.

15. A respirator in accordance with claim 10, wherein said transmitter mount and said receiver mount cooperate to form a lumen receiving region, said transmitter mount and said receiver mount positioning said ultrasound transmitter and said ultrasound receiver relative to said lumen receiving region with said ultrasound transmitter being arranged at a spaced location from said ultrasound receiver such that said ultrasound receiver can receive ultrasound waves transmitted by said ultrasound transmitter and the ultrasound waves pass through said lumen at least in some sections.

\* \* \* \* \*